United States Patent
Ham

(10) Patent No.: US 10,431,346 B2
(45) Date of Patent: Oct. 1, 2019

(54) RADIATION SHIELDING LIQUID FILTER, AND X-RAY IMAGING DEVICE PROVIDED WITH SAME

(71) Applicant: Jae Sang Ham, Seoul (KR)

(72) Inventor: Jae Sang Ham, Seoul (KR)

(*) Notice: Subject to any disclaimer, the term of this patent is extended or adjusted under 35 U.S.C. 154(b) by 198 days.

(21) Appl. No.: 15/544,291

(22) PCT Filed: Feb. 11, 2015

(86) PCT No.: PCT/KR2015/001375
§ 371 (c)(1),
(2) Date: Jul. 18, 2017

(87) PCT Pub. No.: WO2016/117748
PCT Pub. Date: Jul. 28, 2016

(65) Prior Publication Data
US 2017/0372809 A1    Dec. 28, 2017

(30) Foreign Application Priority Data
Jan. 19, 2015   (KR) .................. 10-2015-0008614

(51) Int. Cl.
*G21K 1/10* (2006.01)
*G21K 5/04* (2006.01)
*A61B 6/10* (2006.01)
*G01N 23/04* (2018.01)
*A61B 6/00* (2006.01)
*A61N 5/10* (2006.01)

(52) U.S. Cl.
CPC .................. *G21K 1/10* (2013.01); *A61B 6/10* (2013.01); *A61B 6/107* (2013.01); *A61B 6/4035* (2013.01); *G01N 23/04* (2013.01); *G21K 5/04* (2013.01); *A61N 2005/1095* (2013.01)

(58) Field of Classification Search
CPC ......... A61B 6/10; A61B 6/107; A61B 6/4035; G21K 1/10; G21K 5/04
See application file for complete search history.

(56) References Cited

U.S. PATENT DOCUMENTS

| | | | |
|---|---|---|---|
| 5,966,426 A | 10/1999 | Marra et al. | |
| 2012/0181082 A1* | 7/2012 | Faulkner | H02G 1/08 174/75 R |

FOREIGN PATENT DOCUMENTS

| | | |
|---|---|---|
| EP | 0371699 A1 | 6/1990 |
| JP | 9-329699 A | 12/1997 |
| KR | 10-1145143 B1 | 5/2012 |

(Continued)

OTHER PUBLICATIONS

International Search Report dated Oct. 15, 2015, issued in counterpart Application No. PCT/KR2015/001375. (2 pages).

*Primary Examiner* — David P Porta
*Assistant Examiner* — Fani Boosalis
(74) *Attorney, Agent, or Firm* — Westerman, Hattori, Daniels & Adrian, LLP

(57) ABSTRACT

The purpose of the present invention is to provide: a radiation shielding liquid filter having a radiation shielding effect, a simpler and lighter structure, and various mounting locations so as to protect a surgical patient from exposure to radiation emitted during X-ray imaging using a C-arm, which is a mobile X-ray imaging device, and a stationary X-ray imaging device used during X-ray imaging in a hospital; and an X-ray imaging device provided with the same.

2 Claims, 3 Drawing Sheets

(56) References Cited

FOREIGN PATENT DOCUMENTS

KR 10-1225241 B1 1/2013
WO 2007/095241 A2 8/2007

* cited by examiner

[Fig. 1]
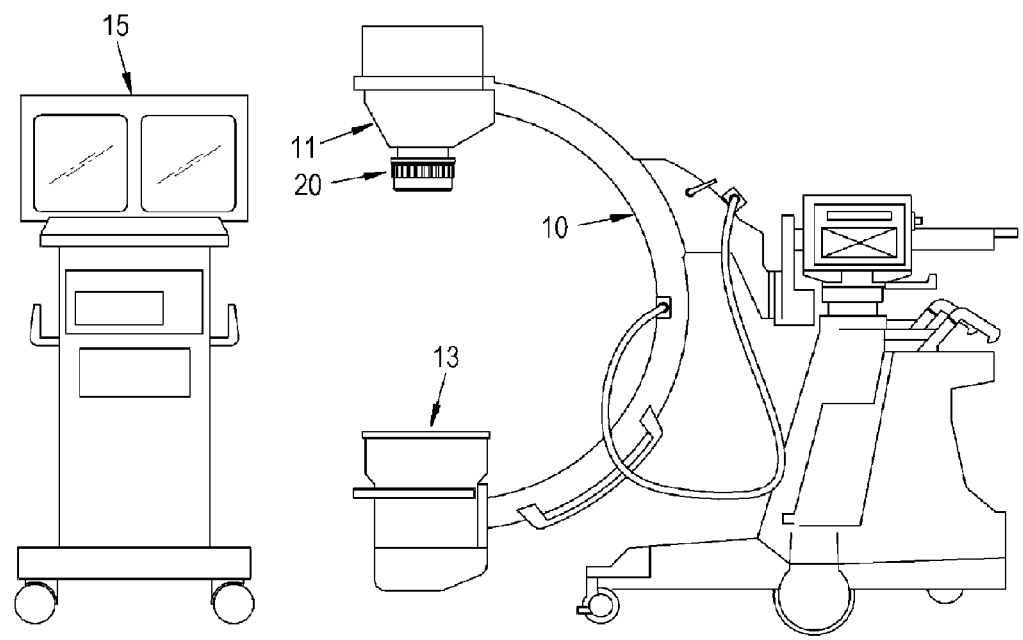

[Fig. 2]
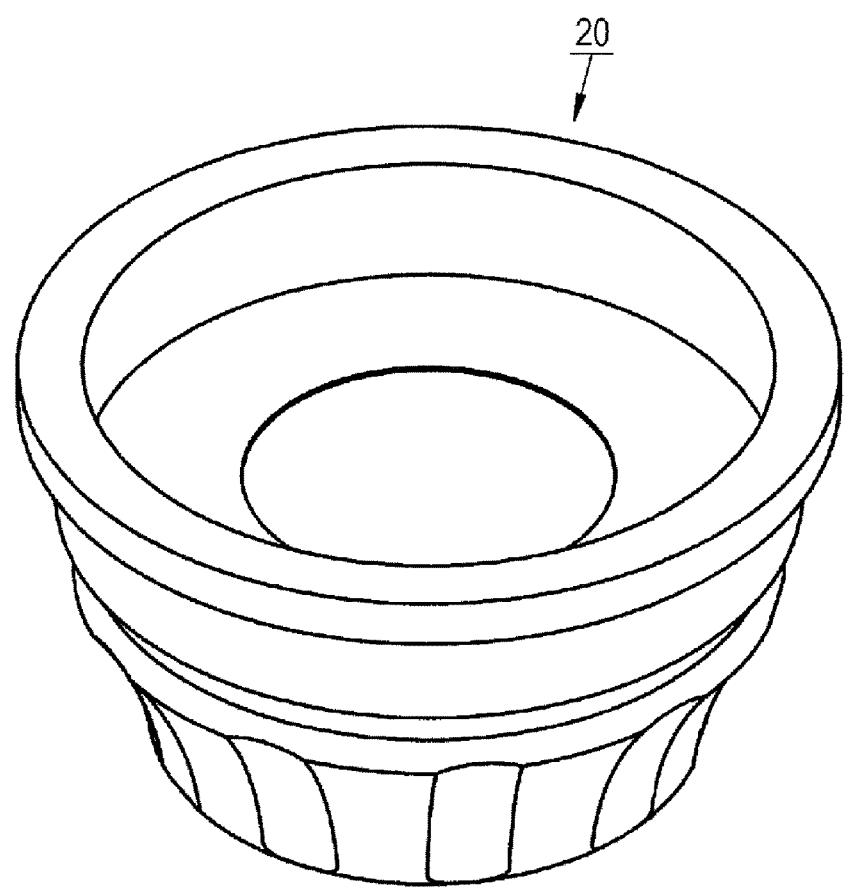

[Fig. 3]
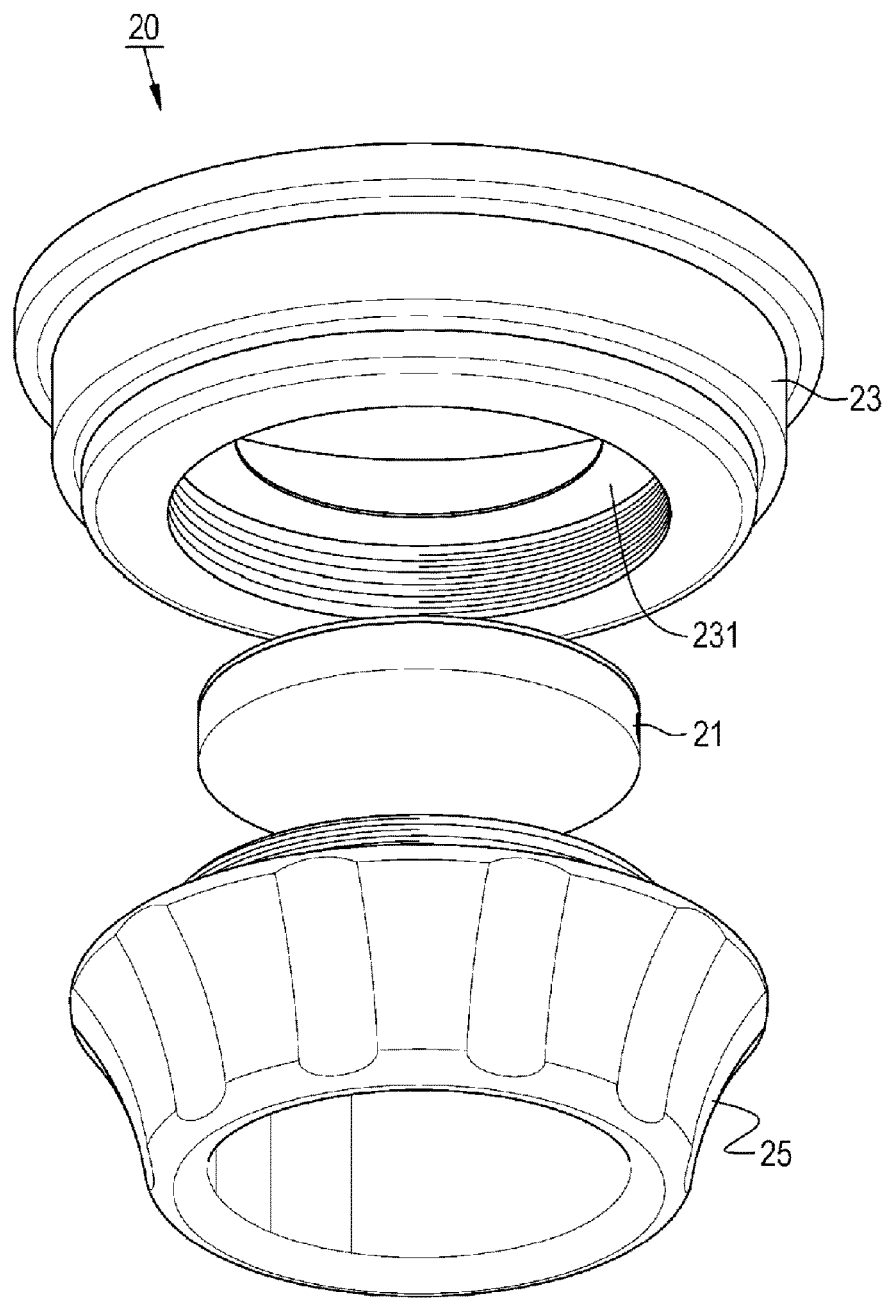

RADIATION SHIELDING LIQUID FILTER, AND X-RAY IMAGING DEVICE PROVIDED WITH SAME

TECHNICAL FIELD

The present invention relates generally to a radiation shielding liquid filter. More particularly, the present invention relates to a radiation shielding liquid filter and an X-ray imaging device provided with same, wherein the liquid filter is capable of providing a simple structure, weight reduction, and various mounting locations.

BACKGROUND ART

In general, a stationary X-ray imaging device is used in an X-ray room in a hospital, and a mobile X-ray imaging device is used in an operating room. The mobile X-ray imaging device is called C-arm because of its shape. The C-arm is a device that captures X-ray images, performs image processing in a computer, and displays a video image in real time on a monitor when a physician in the operating room aligns bones or implants screws or pins while operating on patients with bone fractures, patients with disc problems, or patients with spine related problems, or when the physician examines the bone structure at various angles or visually checks whether the bone is in the correct position when performing manual repositioning (adjusting the bones without surgery) of the fracture. As such, the X-ray imaging device is an essential device especially for orthopedic operations and neurosurgical operations.

The C-arm requires a smaller radiation dose than the stationary X-ray imaging device, but while the C-arm is operated (i.e., while the operator's foot is on the foot switch, about 30 seconds to 1 minute depending on the operator of the X-ray imaging device) during operation, the operator (hereinafter, 'operator' refers to a doctor, a nurse, a surgeon, an operation assistant, an X-ray imaging device operator, etc.) is constantly exposed to radiation. Accordingly, after a major surgical operation that takes several hours, the radiation dose is increased because the operator is exposed to radiation for a long time. As a result, extreme fatigue is caused after surgery, and long-term repeated exposure to radiation causes damage to the human body including cancer, leukemia, etc.

In an effort to reduce the radiation dose to the operator as well as the patient during surgery, the applicant (inventor) of the present invention has developed Korean Patent No. 1145143, entitled "Radiation shield apparatus for X-ray photographing device", and has developed and patented Korean Patent No. 1225241, entitled "Radiation shield apparatus for X-ray photographing device", which has a more compact structure and is capable of significantly reducing the radiation dose.

The present applicant has commercialized patented products currently on the market. The above-patented products have a radiation shielding effect, but they are heavy and the mounting location of the shield apparatus cannot be changed. In addition, actual users have demanded a more compact and more lightweight radiation shielding unit that is capable of being mounted in various locations while providing a radiation shielding effect, so the present applicant has developed the present invention while continuing research and development in order to comply with such practical requests.

DISCLOSURE

Technical Problem

Accordingly, the present invention has been made keeping in mind the above problems occurring in the prior art, and an object of the present invention is to provide a radiation shielding liquid filter and an X-ray imaging device provided with same, wherein the liquid filter is capable of providing a simpler structure, weight reduction, and various mounting locations as well as providing a radiation shielding effect for protecting an operator from exposure to radiation emitted during X-ray imaging from a C-arm, which is a mobile X-ray imaging device, and a stationary X-ray imaging device that are used in the hospital for X-ray imaging.

Technical Solution

In order to accomplish the above object, the present invention provides a radiation shielding liquid filter having a function of shielding radiation emitted from an X-ray imaging device toward an operator to protect the operator from exposure to the radiation, the liquid filter including: a casing filled with a liquid material, the liquid material having a composition of: 10 to 30 parts by weight of silver (Ag) in powder form; 25 to 40 parts by weight of a polymeric dispersant; 45 to 50 parts by weight of water; and 1 to 5 parts by weight of at least one element selected from copper (Cu), aluminum (Al), and mercury (Hg).

A radiation shielding unit of the present invention has a function of shielding radiation emitted toward an operator to protect the operator from exposure to radiation emitted from the X-ray imaging device, wherein the radiation shielding unit includes: an attachment member having a hole formed through a central portion of the attachment member in a vertical direction, and a step formed along a circumference of the hole, the attachment member being provided on a distal end of a tube that is an X-ray generation part of the X-ray imaging device; a liquid filter seated on the step of the attachment member; and a filter holding member having a hole formed through a central portion of the filter holding member in the vertical direction, and screw-coupled to the attachment member, the filter holding member holding the liquid filter seated in the attachment member.

An X-ray imaging device of the present invention has a function of shielding radiation emitted toward an operator to protect the operator from exposure to radiation emitted from the X-ray imaging device, wherein the X-ray imaging device is provided with: a liquid filter including a casing filled with a liquid material, the liquid material having a composition of: 10 to 30 parts by weight of silver (Ag) in powder form; 25 to 40 parts by weight of a polymeric dispersant; 45 to 50 parts by weight of water; and 1 to 5 parts by weight of at least one element selected from copper (Cu), aluminum (Al), and mercury (Hg), wherein the liquid filter is provided between an X-ray generator provided in the X-ray imaging device and a tube emitting X-rays generated by the X-ray generator to a patient.

Advantageous Effects

Since the radiation shielding liquid filter according to the present invention having the above-described features is formed by filling a casing with a liquid shielding material, it is possible to achieve a very compact and simple structure, and weight reduction. In addition, since the casing filled with the liquid shielding material can be mounted on an end portion of a tube from which radiation is emitted, it may be efficiently mounted on an existing X-ray imaging device, and further, it may be also mounted at an appropriate position between a tube and an X-ray generator of a new X-ray imaging device when manufacturing the X-ray imaging device. Thus, it is possible to vary the mounting location of the radiation shielding liquid filter.

Further, as a result of the actual measurement, the radiation dose from a CT scan is about 7 mSV per scan, and the radiation dose from a C-arm is about 3.5 mSV per scan. When the radiation shielding liquid filter according to the present invention is mounted on the end portion of the tube, radiation reflected and scattered after penetrating the patient can be reduced by about 60%. Thus, it is possible to significantly reduce the radiation dose to the operator by shielding 80 to 90% of the total radiation scattered or reflected to the operator.

DESCRIPTION OF DRAWINGS

FIG. 1 is a view showing a C-arm provided with a radiation shielding unit of the present invention.

FIG. 2 is a view showing a state in which the radiation shielding unit is assembled.

FIG. 3 is a view showing a state in which the radiation shielding unit is disassembled.

| <Description of the Reference Numerals in the Drawings> | | | |
|---|---|---|---|
| 10: | C-arm | 11: | tube |
| 13: | detector | 15: | monitor |
| 20: | radiation shielding unit | 231: | step |
| 21: | liquid filter | | |
| 23: | attachment member | | |
| 25: | filter holding member | | |

BEST MODE

The most significant technical feature of a radiation shielding liquid filter and an X-ray imaging device provided with the same according to the present invention is that the filter can be formed in a liquid phase, so that it is possible to reduce weight of the filter and to produce the filter by changing the shape and size thereof according to the demand of a user, and the mounting location of the liquid filter can be varied, so that the liquid filter may be efficiently mounted on a tube of an existing X-ray imaging device, and may be mounted in a new X-ray imaging device when manufacturing the X-ray imaging device.

MODE FOR INVENTION

In general, a C-arm that is a mobile X-ray imaging device includes: a tube 11 that is an X-ray generation part; a detector 13 receiving a captured X-ray image, the tube and the detector being provided at opposite ends of a C-arm frame, respectively; a shaft provided at a middle portion of the frame and serving as a rotary axis of the frame; a control unit having a castor attached to a lower portion of the control unit; and a monitor 15 receiving data from the control unit and displaying the received data as a video image in real time.

A radiation shielding unit 20 according to the present invention is mounted on the tube 11 emitting X-rays generated by an X-ray generator of a stationary X-ray imaging device and a mobile X-ray imaging device to a patient, the radiation shielding unit including: an attachment member 23 coupled to the tube 11; a filter holding member 25 screw-coupled to the attachment member 23; and a liquid filter 21 provided between the attachment member and the filter holding member. The attachment member 23 may be screw-coupled to a distal end of the tube 11, or holes may be formed at locations where the attachment member and the filter holding member face each other such that the radiation shielding unit 20 and the X-ray imaging device are combined using a binding member such as an iron band, an iron cord, etc. However, the method of mounting the radiation shielding unit is not particularly limited.

Both the attachment member 23 and the filter holding member 25 function to protect an operator by shielding radiation scattered toward the operator, so they are made of a material capable of shielding the scattered radiation. Since a material composed of only lead is too heavy, a material including at least one element selected from lead (Pb), aluminum (Al), silicon (Si), titanium (Ti), chromium (Cr), manganese (Mn), iron (Fe), cobalt (Co), nickel (Ni), copper (CU), zinc (Zn), molybdenum (Mo), rhodium (Rh), silver (Ag), tin (Sn), tungsten (W), platinum (Pt), and gold (AU) is used.

The most dangerous thing to the operator during X-ray imaging is that radiation emitted from the X-ray imaging device directly penetrates the operator, or radiation emitted from the tube 11 penetrates a patient and then is reflected to the operator.

The liquid filter 21 significantly reduces the amount of radiation reflected to the operator after penetrating the patient. In addition, one of the important properties required for the liquid filter 21 is to prevent an X-ray image of the patient from being blurred.

The liquid filter 21 includes a casing filled with a liquid material, the liquid material having a composition of 10 to 30 parts by weight of silver (Ag) in particulate powder form, 25 to 40 parts by weight of a polymeric dispersant, 45 to 50 parts by weight of water, and 1 to 5 parts by weight of at least one element selected from copper (Cu), aluminum (Al), and mercury (Hg). The dispersant functions to uniformly spread the metal element including silver (Ag) in particulate powder form so as not to be spread to a certain part of the casing. The dispersant uses a polyoxyethylene sorbitan monooleate.

As shown in FIG. 3, the radiation shielding unit 20 includes the attachment member 23, the filter holding member 25, and the liquid filter 21 placed between the attachment member and the filter holding member. The attachment member 23 is provided with a hole formed through a central portion of the attachment member in a vertical direction, and a step 231 formed along a circumference of the hole, such that the attachment member is mounted on the distal end of tube 11, which is the X-ray generation part of the X-ray imaging device.

The liquid filter 21 is filled in a casing made of a material such as plastic, and is seated on the step 231 formed on an inner surface of the attachment member 23. The filter holding member 25 is provided with a hole formed through a central portion of the filter holding member in the vertical direction and is screwed into a spiral groove formed on an inner circumferential surface of the attachment member 23 such that the attachment member 23, the liquid filter 21, and the filter holding member 23 are integrally assembled. As described above, the radiation shielding unit 20 has a very compact and simple structure, and has very light weight because the three components are assembled together.

One of the structural features of the present invention is that the radiation shielding unit 20 provided with the liquid filter 21 is not only mounted on the distal end of the tube 11 but also can be mounted in various locations. Although not shown in the drawings, the liquid filter 21 itself may be provided integrally within the X-ray imaging device. When the liquid filter is installed in the X-ray imaging device, only the liquid filter 21 is mounted therein. In this case, the liquid filter 21 may be mounted at a position between the X-ray generator and the tube emitting X-rays generated by the X-ray generator to the patient.

Although the preferred embodiment of the present invention have been disclosed for illustrative purposes, those skilled in the art will appreciate that various modifications, additions and substitutions are possible, without departing from the scope and spirit of the invention as disclosed in the accompanying claims. Therefore, the embodiments of the present invention are disclosed only for illustrative purposes and should not be construed as limiting the present invention. The scope of the invention should be determined on the basis of the descriptions in the appended claims, not any specific embodiment, and all equivalents thereof should belong to the scope of the invention.

What is claimed is:

1. An X-ray imaging device with a radiation shielding liquid filter, the radiation shielding liquid filter having a function of shielding radiation emitted from an X-ray imaging device toward an operator to protect the operator from exposure to the radiation, the liquid filter comprising:

a casing filled with a liquid material, the liquid material having a composition of: 10 to 30 parts by weight of silver (Ag) in powder form; 25 to 40 parts by weight of a polymeric dispersant; 45 to 50 parts by weight of water; and 1 to 5 parts by weight of at least one element selected from copper (Cu), aluminum (Al), and mercury (Hg), the X-ray imaging device comprising: a radiation shielding unit, the radiation shielding unit including:

an attachment member having a hole formed through a central portion of the attachment member in a vertical direction, and a step formed along a circumference of the hole, the attachment member being provided on a distal end of a tube that is an X-ray generation part of the X-ray imaging device; and a filter holding member having a hole formed through a central portion of the filter holding member in the vertical direction, and screw-coupled to the attachment member, the filter holding member holding the liquid filter seated in the attachment member, wherein the liquid filter is seated on the step of the attachment member.

2. The X-ray imaging device of claim 1, wherein the liquid filter is provided between an X-ray generator provided in the X-ray imaging device and a tube emitting X-rays generated by the X-ray generator to a patient.

* * * * *